US008831326B2

(12) United States Patent
Nishida et al.

(10) Patent No.: US 8,831,326 B2
(45) Date of Patent: Sep. 9, 2014

(54) METHOD FOR COUNTING COLONIES

(75) Inventors: Takashi Nishida, Gifu-ken (JP); Shenglan Li, Gifu-ken (JP); Chizuka Kai, Tokyo (JP); Kunimitsu Toyoshima, Osaka (JP)

(73) Assignees: Kabushiki Kaisha N-Tech, Gifu-Ken (JP); Kabushiki Kaisha Yakult Honsha, Tokyo (JP); Tohoshoji Kabushiki Kaisha, Osaka (JP)

( * ) Notice: Subject to any disclaimer, the term of this patent is extended or adjusted under 35 U.S.C. 154(b) by 773 days.

(21) Appl. No.: 12/601,544

(22) PCT Filed: May 9, 2008

(86) PCT No.: PCT/JP2008/058626
§ 371 (c)(1),
(2), (4) Date: Nov. 24, 2009

(87) PCT Pub. No.: WO2008/149636
PCT Pub. Date: Dec. 11, 2008

(65) Prior Publication Data
US 2010/0166271 A1    Jul. 1, 2010

(30) Foreign Application Priority Data
Jun. 4, 2007   (JP) .................................. 2007-147919

(51) Int. Cl.
*G06K 9/00* (2006.01)
*C12Q 1/06* (2006.01)
*G06K 9/62* (2006.01)

(52) U.S. Cl.
CPC ......................................... *C12Q 1/06* (2013.01)
USPC ........................................... 382/133; 382/100

(58) Field of Classification Search
USPC ............................................................ 382/133
See application file for complete search history.

(56) References Cited

FOREIGN PATENT DOCUMENTS

| JP | 3-168079 | A |   | 7/1991  |                |
|----|----------|---|---|---------|----------------|
| JP | 7-59556  | A |   | 3/1995  |                |
| JP | 9-121836 | A | * | 5/1997  | ........ C12N 1/34 |
| JP | 9-121836 | A |   | 5/1997  |                |
| JP | 9121836  | A | * | 5/1997  | ........ C12N 1/34 |
| JP | 9-140397 | A |   | 6/1997  |                |
| JP | 2001-22929 | A |   | 1/2001  |                |
| JP | 2003-116593 | A |   | 4/2003  |                |
| JP | 2003-116593 | A | * | 4/2003  | ........ C12Q 1/04 |
| JP | 2003-135095 | A |   | 5/2003  |                |
| JP | 2004-194610 | A |   | 7/2004  |                |
| JP | 2006-345750 | A | * | 12/2006 | ........ C12Q 1/04 |
| JP | 2006-345750 | A |   | 12/2006 |                |

* cited by examiner

*Primary Examiner* — Tran Nguyen
(74) *Attorney, Agent, or Firm* — Seager, Tufte & Wickhem LLC

(57) ABSTRACT

Colonies growing on a culture medium surface may be more accurately counted with reduced variation in the counts obtained by capturing a plurality of images of the entire culture medium surface, wherein successive images are captured following rotation of the culture medium surface relative to the image capture apparatus by n/360 degrees where n is the number of images to be captured; performing data processing on image data of the entire culture medium surface of the petri dish at each specified angle; and the number of colonies in the petri dish is calculated by performing numerical processing on the number of colonies counted separately at each specified angle.

8 Claims, 5 Drawing Sheets

METHOD FOR COUNTING COLONIES

FIELD OF THE INVENTION

The present invention relates to a colony counting method for counting the number of microbial colonies developed after microorganisms such as molds and fungi are cultured in a culture media using a petri dish.

BACKGROUND OF THE INVENTION

In a food industry field, it is necessary to confirm that food products of which the number of microorganisms needs to be counted do not cause problems, or that useful microorganisms are properly grown in the food manufacturing process. As a viable cell detection system used for this confirmation, cultivation-type counting means using a culture medium is often used. For example, there has been used a method of counting the number of microbial colonies using an agar medium as an official method of counting microorganisms. In particular, for counting target products having a low distribution of microorganisms, the above method has been widely used as means by which microorganisms are cultivated in a short time period to develop microbial colonies and the number of microorganisms is counted in an easy and simple manner with a good accuracy.

Alternatively, instead of a conventional method of visually counting the number of colonies developed in an agar medium or the like, there have been proposed several methods of automatically counting the number of colonies by performing data processing on the image of a counting target culture medium taken by a CCD camera or the like. That is, the proposed colony counting methods include a method of counting the number of colonies by identifying the connected colonies by the shape (see Patent Document 1) and a method of counting the number of microorganisms by detecting an peripheral arc of colonial microorganisms using shading of hues (see Patent Document 2).

Further, there has been proposed a method of counting the number of colonies with a good accuracy by performing data processing on a CCD camera image using hues in an easy and simple manner (see Patent Document 3). The present applicant has proposed an inspection method of automatically counting the number of colonies with a good accuracy using a monochrome CCD camera by dividing the colony inspection regions (see Patent Document 4).

However, it has been apparent from past experience that conventional colony counting means provides a different number of colonies for each counting when the number of colonies in the same counting target petri dish is counted if the lighting plan position and the lighting angle with respect to the target petri dish and the distance between the CCD camera and the petri dish and the like are changed. The reason is mainly that colony image data taken by the CCD camera is changed because of the complicate relationship of the relative position of the lighting and the CCD camera and the relative position of the colonies with respect to minute colonies developed and scattered in various depth ranges in agar media and the like, resulting in a variation of automatic colony count in conjunction with data processing method for the image data.

For this reason, the food industry required to have an accurate number of colonies has been seeking a practical colony counting method that ensures stable counting data by eliminating the variations of the number of colonies in the same petri dish.

Patent Document 1: Japanese Laid-Open Patent Publication No. H09-140397

Patent Document 2: Japanese Laid-Open Patent Publication No. 2001-22929

Patent Document 3: Japanese Laid-Open Patent Publication No. 2004-194610

Patent Document 4: Japanese Laid-Open Patent Publication No. 2006-345750

SUMMARY OF THE INVENTION

Problems to be Solved by the Invention

In view of the above problems, the present invention has been made, and an objective of the present invention is to provide a colony counting method capable of obtaining highly reliable and stable colony count values with easy and simple means by eliminating the variation in colony count due to image capturing conditions.

Means for Solving the Problems

The invention according to claim 1 relates to a colony counting method characterized in that, when the number of microbial colonies developed in a culture medium in a petri dish is counted by performing image capturing and data processing on microbial colonies using image capturing means provided in an extension direction of a rotational axis, which is set near a center of the culture medium surface of the petri dish, the petri dish is rotated around the rotational axis by a specified angle obtained by dividing one rotation of the petri dish by a predetermined number, and image data of the entire culture medium surface of the petri dish at the specified angle is acquired by performing image capturing on the entire culture medium surface of the petri dish for each rotation of the petri dish by the specified angle; the number of colonies at each specified angle is counted separately by performing data processing on image data of the entire culture medium surface of the petri dish at the specified angle; and the number of colonies in the petri dish is calculated by performing numerical processing on the number of colonies counted separately at each specified angle.

The invention according to claim 2 relates to a colony counting method characterized in that, when the number of microbial colonies developed in a culture medium in a petri dish is counted by performing image capturing and data processing on microbial colonies using image capturing means provided in an extension direction of a rotational axis, which is set near a center of the culture medium surface of the petri dish, the image capturing means is rotated by a specified angle obtained by dividing one rotation of the petri dish by a predetermined number, and image data of the entire culture medium surface of the petri dish at the specified angle is acquired by performing image capturing on the entire culture medium surface of the petri dish for each rotation of the image capturing means by the specified angle; the number of colonies at each specified angle is counted separately by performing data processing on image data of the entire culture medium surface of the petri dish at the specified angle; and the number of colonies in the petri dish is calculated by performing numerical processing on the number of colonies counted separately at each specified angle.

The invention according to claim 3 relates to the colony counting method according to claim 1, characterized in that, when image capturing is performed on the entire culture medium surface of the petri dish at each specified angle, the image capturing means performs image capturing a plurality of number of times per specified angle and acquires a plurality of images at the one specified angle; data processing is performed on each acquired image data to count the number of colonies at the one specified angle a plurality of number of times; and numerical processing is performed on the number of colonies counted separately at each specified angle to calculate the number of colonies in the petri dish.

The invention according to claim 4 relates to the colony counting method according to claim 2, characterized in that, when image capturing is performed on the entire culture medium surface of the petri dish at each specified angle, the image capturing means performs image capturing a plurality of number of times per specified angle and acquires a plurality of images at the one specified angle; data processing is performed on each acquired image data to count the number of colonies at the one specified angle a plurality of number of times; and numerical processing is performed on the number of colonies counted separately at each specified angle to calculate the number of colonies in the petri dish.

The invention according to claim 5 relates to the colony counting method according to claim 1, characterized in that the petri dish is temporarily stopped for each rotation at the specified angle and the image capturing means performs image capturing on the entire culture medium surface of the petri dish.

The invention according to claim 6 relates to the colony counting method according to claim 2, characterized in that the image capturing means is temporarily stopped for each rotation at the specified angle and the image capturing means performs image capturing on the entire culture medium surface of the petri dish.

Advantages of the Invention

According to the colony counting method in accordance with the invention of claim 1, when the number of colonies is counted by performing image capturing and data processing on microbial colonies developed in a culture medium in a petri dish by image capturing means provided in an extension direction of a rotational axis, which is set near a center of the culture medium surface of the petri dish, the petri dish is rotated around the rotational axis by a specified angle obtained by dividing one rotation of the petri dish by a predetermined number, and image data of the entire culture medium surface of the petri dish at the specified angle is acquired by performing image capturing on the entire culture medium surface of the petri dish for each rotation of the petri dish by the specified angle; the number of colonies at each specified angle is counted separately by performing data processing on image data of the entire culture medium surface of the petri dish at the specified angle; and the number of colonies in the petri dish is calculated by performing numerical processing on the number of colonies counted separately at each specified angle. Therefore, the colony counting method eliminates a problem of adopting a colony count based on biased image data acquired in a state where the lighting and the image capturing means are in a specific position with respect to the petri dish and the colonies. Accordingly, the colony counting method ensures a stable data calculation leveled by a plurality of image capturing conditions.

According to the colony counting method in accordance with the invention of claim 2, when the number of colonies is counted by performing image capturing and data processing on microbial colonies developed in a culture medium in a petri dish by image capturing means provided in an extension direction of a rotational axis, which is set near a center of the culture medium surface of the petri dish, the image capturing means is rotated by a specified angle obtained by dividing one rotation of the petri dish by a predetermined number, and image data of the entire culture medium surface of the petri dish at the specified angle is acquired by performing image capturing on the entire culture medium surface of the petri dish for each rotation of the image capturing means by the specified angle; the number of colonies at each specified angle is counted separately by performing data processing on image data of the entire culture medium surface of the petri dish at the specified angle; and the number of colonies in the petri dish is calculated by performing numerical processing on the number of colonies counted separately at each specified angle. Therefore, the colony counting method eliminates a problem of adopting a colony count based on biased image data acquired in a state where the lighting and the image capturing means are in a specific position with respect to the petri dish and the colonies. Accordingly, the colony counting method ensures a stable data calculation leveled by a plurality of image capturing conditions. In addition, the colony counting method is suitable for a case where the image captured articles cannot be easily rotated because of the size, weight, fragility, and the like.

According to the colony counting method in accordance with the invention of claim 3, in the invention of claim 1, when image capturing is performed on the entire culture medium surface of the petri dish at each specified angle, the image capturing means performs image capturing a plurality of number of times per specified angle and acquires a plurality of images at the one specified angle; data processing is performed on each acquired image data to count the number of colonies at the one specified angle a plurality of number of times; and numerical processing is performed on the number of colonies counted separately at each specified angle to calculate the number of colonies in the petri dish. Therefore, the colony counting method can eliminate the variation of image data due to image capturing conditions and the like occurring at each specified angle by performing image capturing a plurality of number of times and can count the number of colonies in the petri dish more stably.

According to the colony counting method in accordance with the invention of claim 4, in the invention of claim 2, when image capturing is performed on the entire culture medium surface of the petri dish at each specified angle, the image capturing means performs image capturing a plurality of number of times per specified angle and acquires a plurality of images at the one specified angle; data processing is performed on each acquired image data to count the number of colonies at the one specified angle a plurality of number of times; and numerical processing is performed on the number of colonies counted separately at each specified angle to calculate the number of colonies in the petri dish. Therefore, the colony counting method can eliminate the variation of image data due to image capturing conditions and the like occurring at each specified angle by performing image capturing a plurality of number of times and can count the number of colonies in the petri dish more stably.

According to the colony counting method in accordance with the invention of claim 5, in the invention of claim 1, the petri dish is temporarily stopped for each rotation at the specified angle and the image capturing means performs image capturing on the entire culture medium surface of the petri dish. Therefore, the image captured at each specified angle is clear and the data processing performed on the image increases the accuracy of the colony count.

According to the colony counting method in accordance with the invention of claim 6, in the invention of claim 2, the image capturing means is temporarily stopped for each rotation at the specified angle and the image capturing means performs image capturing on the entire culture medium surface of the petri dish. Therefore, the image captured at each specified angle is clear and the data processing performed on the image increases the accuracy of the colony count.

DETAILED DESCRIPTION OF THE PREFERRED EMBODIMENTS

Hereinafter, a colony counting method in accordance with the present invention will be described based on FIGS. 1 to 5. FIG. 1 is a cross-sectional structural view of a colony counting apparatus in accordance with the present invention. FIG. 2 is a top plan view of the apparatus illustrated in FIG. 1. FIG. 3 is a schematic view of a captured image illustrating colonies developed in a culture medium in a petri dish. FIG. 4 is a flowchart illustrating the colony counting process in accordance with the present invention. FIG. 5 is a cross-sectional structural view of a colony counting apparatus in accordance with another embodiment.

First Embodiment

By referring to the cross-sectional structural view of FIG. 1 and the top plan view of FIG. 2, a counting apparatus 50 suitable for implementing the colony counting method of the present invention will be described. This counting apparatus 50 includes a petri dish rotary mounting device 55, an image capturing means (COD camera 7), and a data processing device 9.

The petri dish rotary mounting device 55 includes a rack 17 having a support plate 5 on the upper portion thereof; a transparent rotating plate 22 thereon; and a drive motor 19 thereon. The transparent rotating plate 22 is fixed on a turntable 16 by means such as screws (not illustrated). Further, the turntable 16 is rotatably supported on the support plate 5 by support rollers 23 (illustrated at three positions). A drive belt 21 is provided on the turntable 16 in a tensioned state. The drive of the drive pulley 20 fixed to the drive motor 19 on the support plate 5 is transmitted to the drive belt 21 to be driven. A counting target petri dish 2 (a culture medium 1 of the petri dish) is placed in a substantially rotational center position of the discoid transparent rotating plate 22. A rotational axis C1 is set near the center of a culture medium surface if of the counting target petri dish 2. The rotational axis C1 is orthogonal to the culture medium surface if of the petri dish.

The support plate 5 having the turntable 16 thereon is provided on an upper portion of the illustrated rack 17. A diffusing plate 4 is provided on the support plate 5. The rack 17 includes a lighting device 6 and a parallel plate 18 in the order from below upward therein. The parallel plate 18 serves to guide a light beam from the lighting device 6 upward as a parallel light beam in a stable manner. The diffusing plate 4 serves to uniformly diffuse the light beam so as to accurately take an image of the culture medium 1.

A CCD camera 7 disclosed as an example of the image capturing means is provided above the petri dish 2, namely, in an extension direction of the rotational axis C1. The petri dish 2 is placed on the transparent rotating plate 22 with the petri dish opening 3 facing downward (in an inverted state) and the culture medium 1 therein is lit from below by the lighting device 6. Then, the CCD camera 7 takes an image of the culture medium including a periphery of the petri dish as a transmitted light from a direction of the petri dish bottom surface. According to the illustrated embodiment, the rotational axis C1 is set to the center of the culture medium surface if of the petri dish 2, and the CCD camera 7 is positioned substantially along an extension line of the rotational axis C1 of the petri dish 2. Regarding the positional relationship between the CCD camera and the rotational axis of the petri dish, the CCD camera does not need to be aligned exactly on the extension line, but axial misalignment may be allowed to some extent as long as an image of the entire petri dish can be captured. Moreover, the position of the rotational axis set to the petri dish (the culture medium surface) is not necessarily exact, but is affected by the size (diameter) of the petri dish, the positional misalignment on the transparent rotating plate and the like. For this reason, the rotational axis is set to substantially the center of the petri dish within a range not disturbing the image capturing of the entire petri dish and rotation of the petri dish. In the illustration, the petri dish is placed on the transparent rotating plate with its lid off in an inverted state, but the petri dish may be placed with its lid on, that is, either way is appropriate.

The data processing device 9 is an appropriate computing device such as a personal computer and is connected to the CCD camera 7 through a signal cable 8c. Image data obtained by capturing an image of the petri dish is sent to the data processing device 9, at which data processing (detailed below) is performed to count the number of colonies K in the petri dish. The image of the petri dish and the like taken as needed are displayed on an image monitor 12. Further, a signal cable 8m is provided to connect between the drive motor 19 and the data processing device 9. On the basis of the control of the data processing device 9, the drive motor 19 is driven in conjunction with image capturing by the COD camera 7 and the transparent rotating plate 22 (petri dish 2) is rotated by a predetermined amount.

Support structure of the illustrated COD camera 7 is omitted from the drawing. As the image capturing means, not only the CCD camera of the embodiment but also a well known device such as a CMOS image sensor can be used. A configuration where when an image of the culture medium 1 is captured, the petri dish opening 3 is positioned to face downward and is lit from below is illustrated above. However, the petri dish 1 can be positioned to face upward and the position of the lighting device 6 and the COD camera 7 can be inverted upside down, and thus the present invention is not particularly limited to this illustrated embodiment. In the drawing, reference character 2a denotes a petri dish side wall.

FIG. 3 is an example of a captured image 14 when an image of the bottom surface of the petri dish 2 is captured by the CCD camera 7. The culture medium 1 is inside the petri dish side wall 2a, where counting target microbial colonies K are developed in various forms. According to the colony counting method in accordance with the embodiments of the present invention, a colony counting region 13 inside the petri dish side wall 2a is divided into a central image region 10 occupying the central portion thereof and a peripheral image region 11 provided outside thereof. As illustrated in the drawing, an image of the entire petri dish (entire culture medium surface 1f) is taken by the CCD camera 7, and is fetched as image data by the data processing device 9.

The dimension of the central image region 10 and the peripheral image region 11 to the inner diameter of the petri dish side wall 2a or the ratio therebetween is not particularly specified. On the basis of past experience, the central image region 10 is selected from a region which is less affected by the petri dish side wall 2a and where favorable images can be acquired. The peripheral image region 11 is selected from a region which is close to the petri dish side wall 2a and where it is different to count the number of colonies K from a captured image.

According to the flowchart illustrated in FIG. 4, the entire colony counting method will be described. First, in an angular division setting (J0), a predetermined number for dividing an angle of 360°, which corresponds to one rotation of the petri dish, is set. In the following embodiment, the colony count corresponding to the number of divisions (corresponding to the predetermined number) is set to 6 (predetermined number=6), which is considered to be performed relatively efficiently for the balance between image capturing and data processing. That is, the colony counting method is configured in such a manner that 60° is set to the specified angle, and each time the petri dish is rotated and stopped around the rotational axis C1 by this specified angle, the CCD camera 7 performs image capturing on the entire culture medium surface. Hereinafter, description is made by taking an example of six divisions (predetermined number=6).

The CCD camera 7 performs a first image capturing of the petri dish placed on the transparent rotating plate 22 (Ji=J1). Then, image data 14 (see FIG. 3) of an image of the entire petri dish is transmitted through the signal cable 8c and inputted to the data processing device 9 (S1), at which data processing (detailed later) is performed to count the number of colonies at the specified angle. Then, after the petri dish is rotated by a specified angle (60°) and stopped, a second image capturing of the petri dish rotated by 60° from the first position is performed (J1=J2). Subsequently, the petri dish is rotated around the rotational axis thereof by a specified angle and temporarily stopped at each specified angle, and then an image is taken at each specified angle and the number of colonies is counted, which continues in sequence.

Then, a counting target count image is generated from the image data of the captured image 14 inputted to the data processing device 9 (S2). In the image data processing of the captured image 14, as illustrated in FIG. 3, a counting region 13 for counting the number of colonies K is determined inside the petri dish side wall 2a based on the preset conditions (S3). Meanwhile, the counting region 13 is divided into the peripheral image region 11 susceptible to data disturbance due to light reflected from the petri dish 2 and the like and the central image region 10 ensuring stable data (S4). Then, pre-processing of image data and counting means adapted to each of the image regions 10 and 11 are used to count the number of colonies separately (S5 and S6).

For example, regarding the image data in the peripheral image region 11, which is close to the petri dish side wall 2a and susceptible to data disturbance due to reflected light and the like, the number of colonies is counted using a preliminarily specified threshold to generate a binary image of the data. In addition, regarding the image data in the central image region 10, which occupies a major portion of the area of the counting region 13 and where data is stable, the number of colonies K is counted using a digitizing method based on a discriminant analysis method of automatically determining a threshold so as to emphasize the difference between the counting target colonies K and its background culture medium.

The colony count value in the peripheral image region 11 and the colony count value in the central image region 10 are integrated for each region (S7). Then, the number of colonies in the entire counting region 13 at the specified angle from the count values integrated for each region is counted and acquired (S8), and is recorded in the data processing device 9 as data of the number of colonies at the specified angle (S9).

When the number of colonies is counted from the image data of the captured image 14, a well known counting method including the aforementioned method (Patent Document 4 (Japanese Patent Laid-Open No. 2006-345750) disclosed in Background Art) is applied.

Then, a confirmation is made as to whether the total number of colony count value for each specified angle accumulated in step S9 of recording a colony count value at an individual angle reaches the number of divisions set in step J0 (S10). According to the present embodiment, a confirmation is made as to whether the total number reaches 6.

If the total number has not reached 6, the petri dish is further rotated by 60° (S11), and a second image of the counting target petri dish is taken (J1=J2) to acquire the captured image 14. Then data processing of counting the number of colonies K continues to be performed from the step (S1) of inputting captured image data to the step (S9) of recording the colony count value at each specified angle as illustrated in the flowchart.

Subsequently, the process of counting the number of colonies at each specified angle continues in sequence. When a confirmation is made that the total number of colony count value at each specified angle accumulated in step of recording a colony count value at an individual angle has reached 6, the same value as the number of divisions (predetermined number), namely, the sixth image capturing (300°) is performed, the image capturing and colony counting for the petri dish are terminated.

Then, numerical processing is performed on six colony count values each at an angle of 0°, 60°, 120°, 180°, 240°, and 300°, which have been recorded in the data processing device 9, to calculate the final number of colonies for the petri dish (S12). According to the present embodiment, the final colony count for the petri dish is determined by calculating an average value of the six colony count values from the first image capturing (0°) to the sixth image capturing (300°). Subsequently, the colony counting target petri dish is changed to another petri dish, and then the colony counting starting with 0° and data recording for each specified angle 60° are performed to count the number of colonies for each petri dish in sequence. When an image of the petri dish is taken, the first image capturing may be performed at an angle of 60° and the sixth image capturing may be performed at an angle of 360°.

According to the present embodiment, an angle of 360° is divided by 6, but the divisor is not particularly limited to 6. In consideration of increased accuracy of the colony counting and the colony count following the image capturing of the petri dish, the number of colonies can be counted by dividing one rotation of the petri dish by a desired number of divisions (predetermined number) and rotating the petri dish by the specified angle based on the number of divisions. According to the colony counting method of the present invention, a calculated colony count may contain fractional numbers, which can be selected freely depending on the purpose of using the calculated colony count from whether data with fractional numbers is used as is or the number can be rounded to an integer to be used.

The colony counting method of the present embodiment eliminates a problem of adopting a colony count based on biased image data acquired in a state where the lighting and various cameras are in a specific position with respect to the petri dish and the colonies, as often pointed out. That is, the method ensures a stable data calculation leveled by a plurality of image capturing conditions. In particular, rotation is temporarily stopped by a specified angle and thus, an image captured at each specified angle is clear and the data processing performed on the image increases the accuracy of the colony count. Further, a stabilized colony count and increased reliability clarify the correlation between the test conditions for microorganisms and the like and the number of colonies, clarifies the guideline for technological development and investigation of the problem and the like for microorganisms, and thus is effective in accelerating technological research activities.

Second Embodiment

According to a second embodiment, the CCD camera 7 performs image capturing of a plurality of number of times at each specified angle obtained by the number of divisions (predetermined number) corresponding to one rotation described in the first embodiment. Then, data of a plurality of images of the entire culture medium surface at the one specified angle are acquired. Then, data processing by the aforementioned colony counting method illustrated in FIG. 3 is performed on data of each of the images of the entire culture medium surface at the acquired one specified angle and the number of colonies at one specified angle is counted for a plurality of number of times. Then, numerical processing is performed on the number of colonies counted separately at each specified angle to calculate the number of colonies in the petri dish. In the second embodiment, perform image capturing on a petri dish in step Ji in the flowchart of FIG. 4 means "perform image capturing on a petri dish for a plurality of number of times".

For example, assuming that the number of divisions (predetermined number) is 6, the corresponding specified angle is 60°. At the image capturing (0°), the image is taken five times. Then, at the second image capturing (60°), the image is also taken five times when the petri dish is rotated at a specified angle of 60°. Subsequently, at the third image capturing (120°), the image is also taken five times, and finally at the sixth image capturing (300°), the image is also taken five times. Then, the number of colonies is counted for each of a total of 30 pieces of image data of the entire culture medium surface acquired in this manner. As a result, 30 colony count values for each of the petri dish are generated. Then, numerical processing is performed on the 30 colony count values to calculate an average value thereof. This average value is determined as the calculated colony count of the counting target petri dish.

Alternatively, five colony count values obtained from the data of five images data of the entire culture medium surface at each specified angle are averaged to tentatively obtain the calculated number of colonies at one specified angle. Then, the calculated numbers of colonies at all specified angles may be obtained to calculate the average of these numbers.

Moreover, the number of colonies can be calculated by performing various kinds of data processing depending on the use purpose in such a manner that peculiar numerical data having a difference of 5% or greater from the average of the five colony count values counted at each specified angle is removed, and the average of the colony count of the remaining data at the specified angle is calculated, and the average of the entire colony count is calculated to set the value as the number of colonies in the counting target petri dish. In addition, the reliability of the calculated numerical values can also be increased by performing an appropriate screening to select numerical data. The number of images taken at one specified angle can be appropriately changed depending on the colony counting purpose or condition. According to the second embodiment, the variation occurring at each specified angle due to the image capturing condition or the like can be eliminated by capturing the image a plurality of number of times, and the number of colonies in the petri dish can be counted more stably.

Third Embodiment

According to a third embodiment, unlike the first embodiment, the rotation of the petri dish is not stopped temporarily at specified angles, but an image of the petri dish is captured at each specified angle while the petri dish is being rotated continuously and data processing is performed on the acquired image data to count and record the number of colonies. Then, these colony count values are used to calculate the number of colonies in the counting target petri dish. The colony counting method, the data processing, and the numerical processing are based on those in the first embodiment. By doing so, the petri dish does not need to be temporarily stopped, and thereby the number of counts of the petri dish per unit time can be increased. However, since image capturing is performed while the petri dish is being rotated, the accuracy of the image processing for the colony counting method needs to be considered.

Fourth Embodiment

According to a fourth embodiment, the counting target petri dish is not rotated, but the image capturing means is rotated for image capturing and counting. As understood from the cross-sectional structural view of FIG. 5, a counting apparatus 60 is configured to include a petri dish mounting device 65, an image capturing means (CCD camera 7), a rotating image capturing unit 66, and a data processing device 9.

The petri dish mounting device 65 includes a rack 17, a support plate 5 provided on an upper portion thereof and a diffusing plate 4 on the support plate 5. The rack 17 has in it a lighting device 6 and a parallel plate 18 in the order from below. The support plate 5 has leg portions 5h thereon and a retention plate 5b is connected to the upper portion of the leg portions 5h.

The rotating image capturing unit 66 is provided on the retention plate 5b. The rotating image capturing unit 66 includes a turntable 16, a rotating plate 22r, and a drive motor 19. The discoid rotating plate 22r is fixed on a turntable 16 by means such as screws (not illustrated). Further, the turntable 16 is rotatably supported on the retention plate 5b by support rollers 23. A drive belt 21 is provided on the turntable 16 in a tensioned state. The drive of the drive pulley 20 fixed to the drive motor 19 on the retention plate 5b is transmitted to the drive belt 21 to be driven. The CCD camera 7 serving as the image capturing means is incorporated in the center position of the discoid rotating plate 22r.

The CCD camera 7 (image capturing means) is provided in an extension direction of the rotational axis C1 when the rotational axis C1 is set to be near the center of the counting target petri dish 2 (culture medium surface if of the petri dish). According to the present embodiment, the rotational axis C2 on the image capturing means side is set to be orthogonal to the center position of the rotating plate 22r and substantially matches the rotational axis C1 set near the center of the culture medium surface of the petri dish. Obviously, because of the same reason as described in the first embodiment, the positional relationship between the rotational axis C1 of the petri dish and the rotational axis (rotational axis C2) on the CCD camera side is not necessarily exact on the extension line, but axial misalignment is allowed to some extent as long as an image of the entire petri dish can be captured. Likewise, the position of the rotational axis C1 set to the petri dish (the culture medium surface) is not necessarily exact, but is affected by the size (diameter) of the petri dish, the positional misalignment of the petri dish placed on the diffusing plate 4 of FIG. 5 and the like. For this reason, the rotational axis C1 of the petri dish is set to substantially the center of the petri dish within a range not disturbing image capturing of the entire petri dish and rotation of the petri dish. The detail of the image capturing means and data processing device 9 in accordance with the fourth embodiment is the same as that of the first embodiment and thus the description is omitted. The same reference numerals or characters are assigned to the components common to those in FIG. 1 and other drawings.

The colony counting method using the counting apparatus 60 disclosed in FIG. 5 as the fourth embodiment is substantially the same as that of the first embodiment illustrated by the flowchart of FIG. 4. In this case, step S11 is changed from rotating petri dish to "rotating camera". Moreover, the colony counting method using the counting apparatus 60 in accordance with the present embodiment can also support the second embodiment in which the image capturing means performs image capturing of a plurality of number of times at each specified angle, the third embodiment in which image capturing is performed by continuously rotating the image capturing means instead of the petri dish, and other combination of numerical selection and average calculation.

According to the fourth embodiment, an article of which image is to be captured such as the petri dish is fixed, and the image capturing means side can be rotated. For this reason, the present embodiment is suitable for image capturing and counting articles which cannot be easily rotated because of the size, weight, fragility, and the like. For example, assume a situation of capturing image of what is cultured in a liquid culture medium and the like from above. In the illustration, the petri dish is placed on the diffusing plate with its lid off in an inverted state, but the petri dish may be placed with its lid on, that is either way is appropriate.

According to the above first to fourth embodiments, the image capturing condition is leveled by dividing the petri dish image capturing position into equal angles. As a result, the petri dish image capturing position relies on a chance that is determined by the first image capturing position. In light of this, first, the number of colonies is tentatively counted at each specified angle by rotating the petri dish. For example, of the above angles, image capturing and colony counting are performed by a separately specified number of times at an angle near the angle at which the most number of colonies is counted. Then, data processing is performed on the colony count data to set the number of colonies in the inspection target petri dish. This method thus can count as many number of colonies as close to reality. As described above, image capturing a plurality of images and colony counting are performed under a desirable condition depending on the purpose of using count data about the number of colonies. Then, data processing is performed on the plurality of count values to count the number of colonies.

As the colony counting means in accordance with the present invention, the description in FIG. 4 focuses on an embodiment in which each inspection region is divided into the peripheral image region 11 and the central image region 10 to perform colony counting of captured image and data processing. The present invention is not limited to the above data processing of the colony count of the captured image, but can also count the number of colonies using various kinds of captured image data processing means.

That is, a principal objective of the present invention is that the counting target petri dish or the image capturing means is rotated and the image capturing means takes a plurality of images of the petri dish; and then data processing is performed on the image data of the plurality of captured images to obtain a stable colony count value. Therefore, not only the illustrated colony counting method but also various kinds of data processing means and counting methods can be adopted within the scope and spirit of the present invention.

Moreover, the description of the present invention focuses on the method of counting the number of colonies K in a culture medium using a petri dish, but the present invention can be applied to other method of counting number of colonies developed in a culture medium using a plastic sheet instead of the petri dish.

EXAMPLES

The inventors attempted to count the number of colonies in the petri dish in which three kinds of fungi A, B, and C were cultured using the colony counting method in accordance with the embodiments detailed herein. The fungus kind A corresponded to the petri dishes with sample numbers 1, 2, 3, and 4. The fungus kind B corresponded to the petri dishes with sample numbers 5, 6, 7, and 8. The fungus kind C corresponded to the petri dishes with sample numbers 9, 10, 11, and 12. The details of the count results are listed in Table 1.

The uppermost line of Table 1 lists one-part division, two-part division, four-part division, six-part division, eight-part division, twelve-part division, and fifteen-part division, each of which indicates the number of divisions, namely, predetermined number, when image capturing was performed in one rotation of the petri dish corresponded to 360°. The one-part division means that image capturing was performed on the counting target petri dish only at one position without rotating the petri dish. For example, in the case of the six-part division, an angle of 360° was divided by 6, which is the number of divisions (predetermined number), and the quotient 60° was used as the specified angle. Each time the petri dish was rotated by the specified angle of 60°, image capturing was performed on the same petri dish six times under six different conditions to count the number of colonies. The same was applied to the other number of divisions. In the table, each parenthesized degree following the number of divisions is the specified angle corresponding to the number of divisions.

In the colony counting method illustrated in Table 1, rotation was temporarily stopped at each specified angle and image capturing was performed four times. A total of four pieces of image data of the entire culture medium surface per specified angle were obtained. The obtained image data was used to average and count the number of colonies in the counting target petri dish. For example, when the number of division was 6 and the specified angle was 60°, 24 pieces of image data were obtained. In Table 1, each petri dish with a sample number had "count" which indicated a count result for each number of divisions. Each % numerals written in the lower line of the petri dish with a sample number is a percentage indication of the ratio of "each colony count" to "the colony count divided by 15".

For example, for sample number 1, the petri dish was rotated and stopped by a specified angle of 24° as the fifteen-part division and image capturing was performed four times, each at the rotational position. Then, the average colony count was 177.2. In contrast to this, in the case of the one-part division where the petri dish is not rotated, the colony count was 179.5. The ratio was thus 101.3%. Likewise, in the case of the six-part division, the colony count was 176.3 and the ratio was 99.5%. The bottom three lines in Table 1 list the maximum, the minimum, and the standard deviation of the percentage indication of the ratio of the colony count of the one to twelve-part divisions for each sample number to the colony count of the fifteen-part division.

TABLE 1

| FUNGUS KIND | SAMPLE NUMBER | UNIT | ONE-PART DIVISION (360°) | TWO-PART DIVISION (180°) | FOUR-PART DIVISION (90°) | SIX-PART DIVISION (60°) | EIGHT-PART DIVISION (45°) | TWELVE-PART DIVISION (30°) | FIFTEEN-PART DIVISION (24°) |
|---|---|---|---|---|---|---|---|---|---|
| A | 1 | COUNT | 179.5 | 175.6 | 176.2 | 176.3 | 177.1 | 178.1 | 177.2 |
|  |  | % | 101.3 | 99.1 | 99.4 | 99.5 | 99.9 | 100.5 | 100.0 |
|  | 2 | COUNT | 200.8 | 196.7 | 196.7 | 196.1 | 197.6 | 197.2 | 196.5 |
|  |  | % | 102.2 | 100.1 | 100.1 | 99.8 | 100.6 | 100.4 | 100.0 |
|  | 3 | COUNT | 193.0 | 189.5 | 190.5 | 190.7 | 190.7 | 189.7 | 189.7 |
|  |  | % | 101.7 | 99.9 | 100.4 | 100.5 | 100.5 | 100.0 | 100.0 |
|  | 4 | COUNT | 135.0 | 133.1 | 131.4 | 132.1 | 132.3 | 131.8 | 132.3 |
|  |  | % | 102.0 | 100.6 | 99.3 | 99.8 | 100.0 | 99.6 | 100.0 |
| B | 5 | COUNT | 256.0 | 252.7 | 253.2 | 253.0 | 253.7 | 253.7 | 253.5 |
|  |  | % | 101.0 | 99.7 | 99.9 | 99.8 | 100.1 | 100.1 | 100.0 |
|  | 6 | COUNT | 181.8 | 180.6 | 181.4 | 180.7 | 180.6 | 180.2 | 180.6 |
|  |  | % | 100.7 | 100.0 | 100.4 | 100.1 | 100.0 | 99.8 | 100.0 |
|  | 7 | COUNT | 83.8 | 84.0 | 83.2 | 83.0 | 83.7 | 83.7 | 84.3 |
|  |  | % | 99.4 | 99.6 | 98.7 | 98.5 | 99.3 | 99.3 | 100.0 |
|  | 8 | COUNT | 93.5 | 95.5 | 94.5 | 94.0 | 95.0 | 95.2 | 95.0 |
|  |  | % | 98.4 | 100.5 | 99.5 | 98.9 | 100.0 | 100.2 | 100.0 |
| C | 9 | COUNT | 268.8 | 274.1 | 272.2 | 274.1 | 272.2 | 271.1 | 272.7 |
|  |  | % | 98.6 | 100.5 | 99.8 | 100.5 | 99.8 | 99.4 | 100.0 |
|  | 10 | COUNT | 226.3 | 229.0 | 229.4 | 228.7 | 228.0 | 230.4 | 230.2 |
|  |  | % | 98.3 | 99.5 | 99.7 | 99.3 | 99.0 | 100.1 | 100.0 |
|  | 11 | COUNT | 251.5 | 255.3 | 253.6 | 252.1 | 253.6 | 253.3 | 252.4 |
|  |  | % | 99.6 | 101.1 | 100.5 | 99.9 | 100.5 | 100.4 | 100.0 |
|  | 12 | COUNT | 194.5 | 191.3 | 192.4 | 192.4 | 192.0 | 194.2 | 196.0 |
|  |  | % | 99.2 | 97.6 | 98.2 | 98.2 | 98.0 | 99.1 | 100.0 |
| MAXIMUM OF % |  | % | 102.2 | 101.1 | 100.5 | 100.5 | 100.6 | 100.5 | 100.0 |
| MINIMUM OF % |  | % | 98.3 | 97.6 | 98.2 | 98.2 | 98.0 | 99.1 | 100.0 |
| STANDARD DEVIATION OF % |  | % | 1.45 | 0.91 | 0.71 | 0.74 | 0.74 | 0.46 | 0.00 |

It is understood from the above results that the percentage indication of the one-part division where the petri dish was not rotated indicates a large swing width such as the maximum of 102.2% and the minimum of 98.3%. Moreover, when the standard deviation was calculated from the percentage indication values of sample numbers 1 to 12 for each number of divisions, the percentage indication of the one-part division where the petri dish was not rotated indicates the largest value.

According to the swing width and the standard deviation based on the percentage indication of the colony count, the colony count obtained without rotating the petri dish had a larger variation than the colony count obtained by rotating the petri dish and performing image capturing under many different conditions. This implies that the colony counting method in accordance with the present invention where the number of colonies is counted by rotating the petri dish provides more stable count data than the conventional method where image capturing is performed without rotating the colony counting target petri dish and the number of colonies is counted.

Moreover, when the counting accuracy of the colony count is compared by changing the number of divisions, the four-part division or the six-part division indicates a substantially equal value with a small swing width and standard deviation, and the eight or more-part division indicates a less increase in counting accuracy in comparison with an increase in workload such as image capturing and image data processing. For this reason, depending on the counting target microorganisms, the culture conditions, and the purpose of using colony count data, the four-part division or the six-part division is the number of divisions suitable for efficient colony counting.

DESCRIPTION OF SYMBOLS

Figure 1:
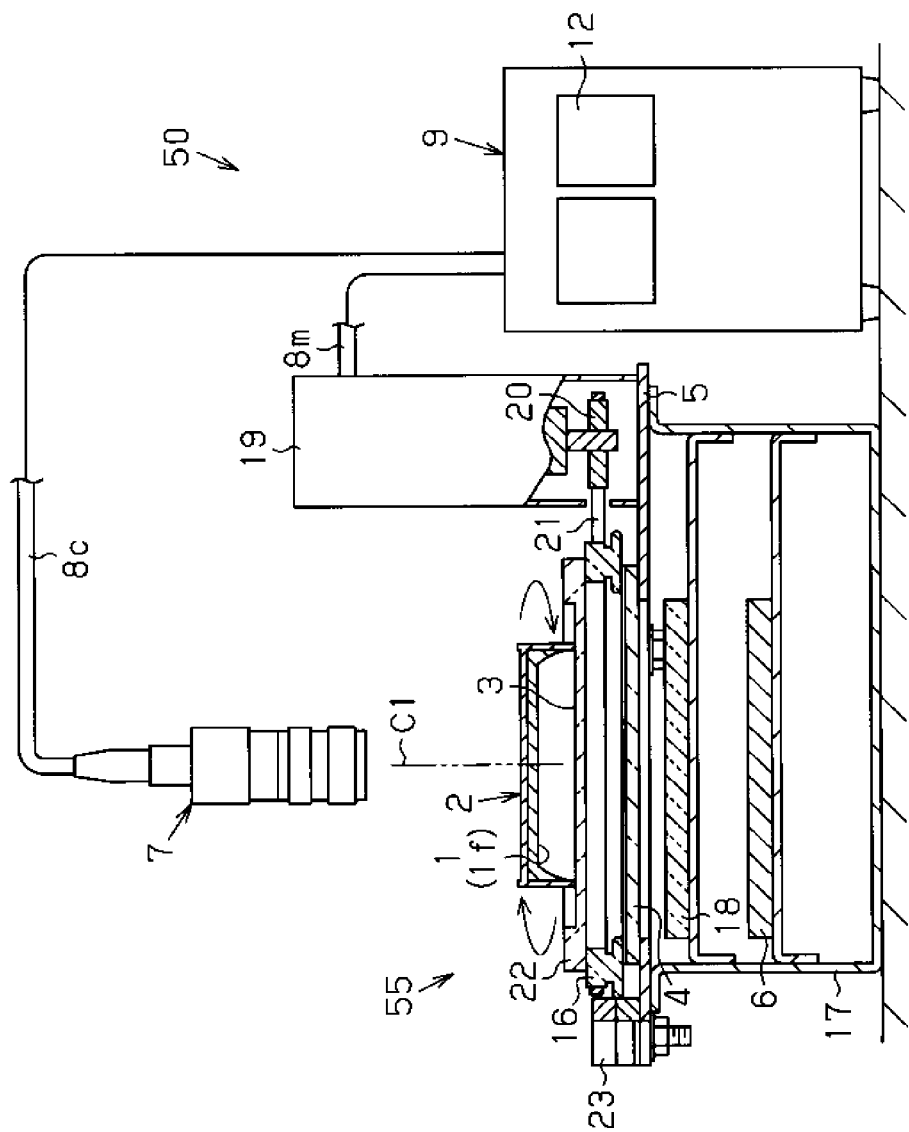
FIG. 1 is a cross-sectional structural view of a colony counting apparatus in accordance with the present invention.
Figure 2:
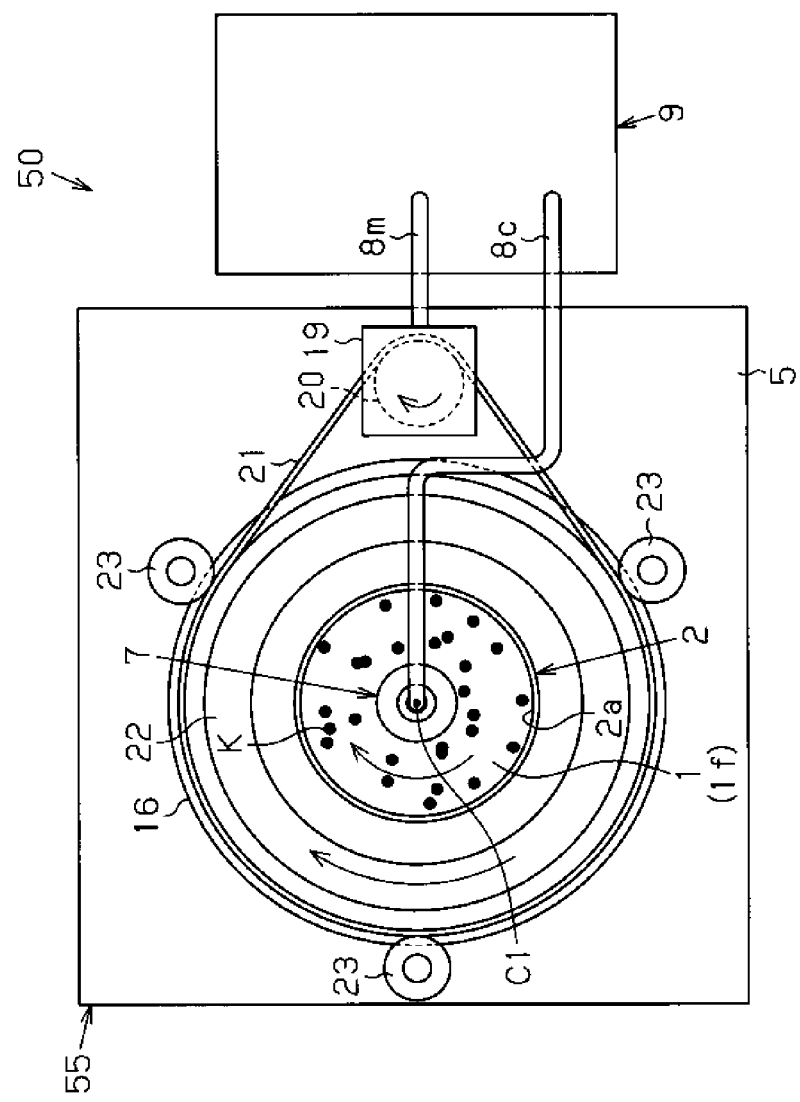
FIG. 2 is a top plan view of the apparatus illustrated in FIG. 1.
Figure 3:
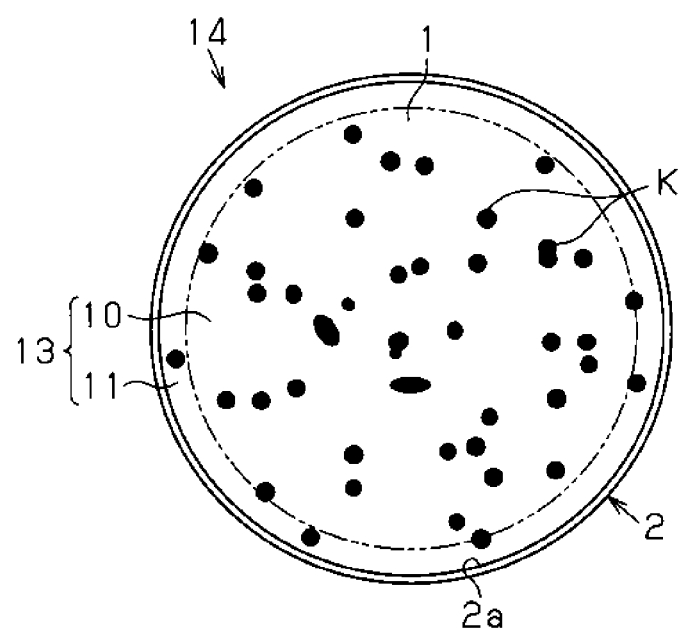
FIG. 3 is a schematic view of a captured image, illustrating colonies developed in a culture medium in a petri dish.
Figure 4:
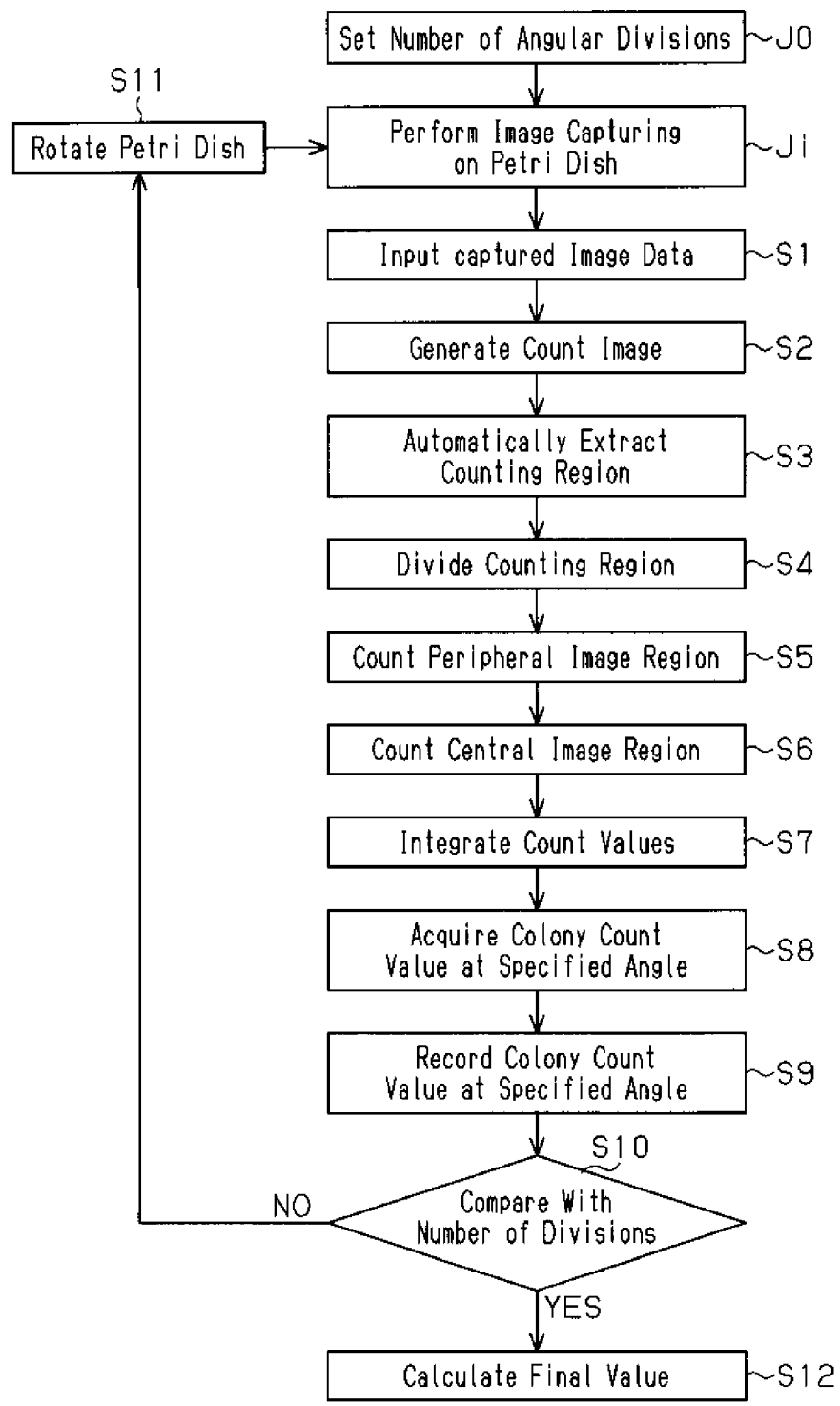
FIG. 4 is a flowchart showing a colony counting process in accordance with the present invention.
Figure 5:
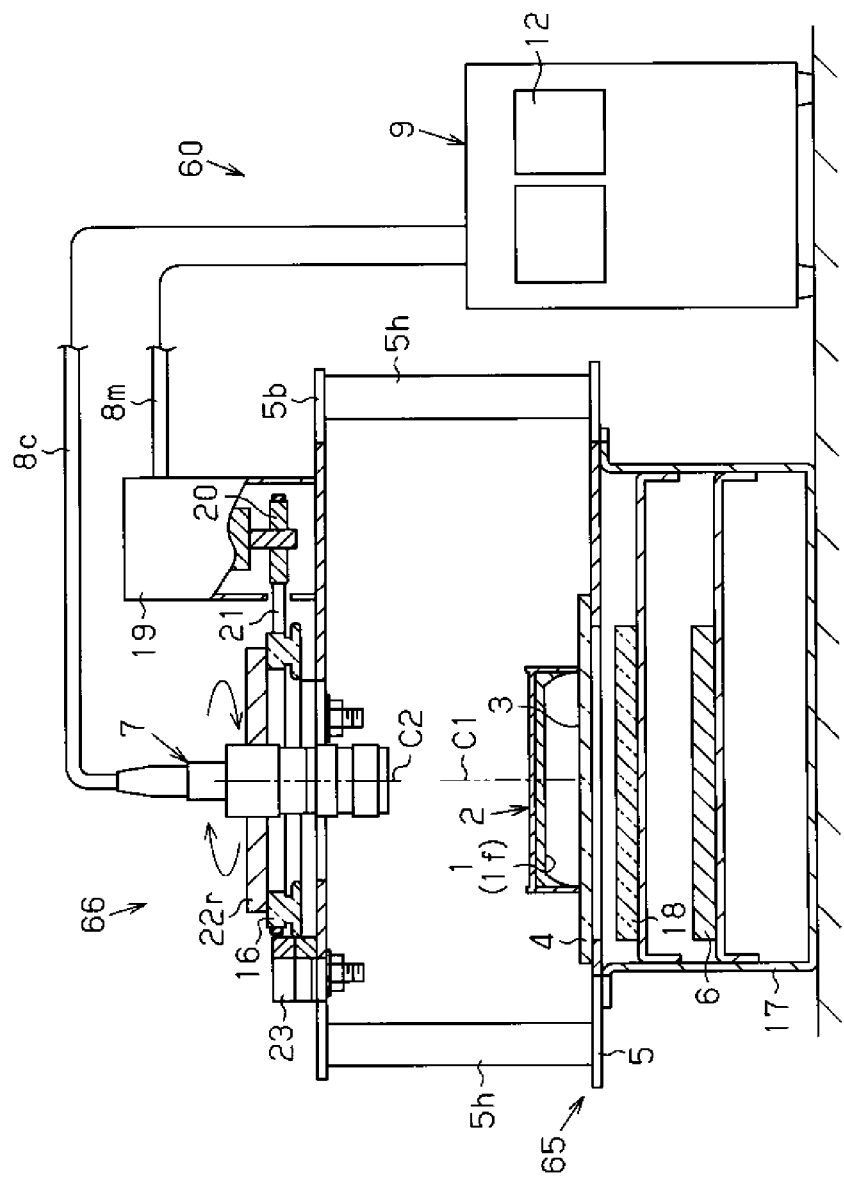
FIG. 5 is a cross-sectional structural view of a colony counting apparatus in accordance with another embodiment.

1 Culture Medium
2 Petri Dish
2a Petri Dish Side Wall
3 Petri Dish Opening
4 Diffusing Plate
5 Support Plate
6 Lighting Device
7 COD Camera (Image Capturing Means)
8c, 8m Signal Cable
9 Data Processing Device
10 Central Image Region
11 Peripheral Image Region
12 Image Monitor
13 Counting Region
14 Captured Image
16 Turntable
17 Rack
18 Parallel Plate
19 Drive Motor 20 Drive Pulley
21 Drive Belt
22 Transparent Rotating Plate
23 Support Roller
50, 60 Counting Apparatus
55 Petri Dish Rotary Mounting Device
65 Petri Dish Mounting Device
66 Rotating Image Capturing Unit
C1 Rotational Axis Of The Petri Dish
C2 Rotational Axis Of The Image Capturing Means
K Colony
J0 Set Number Of Angular Divisions
Ji Perform Image Capturing On Petri Dish
S1 Input Captured Image Data
S2 Generate Count Image
S3 Automatically Extract Counting Region
S4 Divide Counting Region
S5 Count Peripheral Image Region
S6 Count Central Image Region
S7 Integrate Count Values
S8 Acquire Colony Count Value At Specified Angle
S9 Record Colony Count Value At Specified Angle
S10 Compare With Number Of Divisions
S11 Rotate Petri Dish
S12 Calculate Final Value

The invention claimed is:

1. A process for using an imaging apparatus to count the number of colonies on a culture medium surface comprising the steps of:
positioning a petri dish having a culture medium surface and a colony to be counted in an imaging apparatus;
imaging the entire culture medium surface of the petri dish using the imaging apparatus;
rotating the petri dish around a rotational axis within the imaging apparatus by 360/n degrees, where n is a positive integer;
imaging the entire culture medium surface of the petri dish at that rotational position;
repeating the rotating and imaging steps n−1 times;
processing the image data of the entire culture medium surface of the petri dish to count the number of colonies, wherein a counting region for the counting the number of colonies is determined to be the whole petri dish inside the side wall, and the number of colonies in the counting region at a specified angle is counted and acquired;
acquiring a colony count value for each of the n entire culture medium surface images; and
combining and averaging the number of colonies counted for each of the entire culture medium surface images in the petri dish to obtain a colony count for the culture medium surface within the petri dish.

2. The process according to claim 1, wherein when image capturing is performed on the entire culture medium surface of the petri dish at each specified angle,
the imaging apparatus performs image capturing a plurality of times per specified angle and acquires a plurality of images at each specified angle;
data processing is performed on each acquired image data to count the number of colonies at each specified angle a plurality of number of times; and
numerical processing is performed on the number of colonies counted separately at each specified angle to calculate the number of colonies in the petri dish.

3. The process according to claim 1, wherein the petri dish is temporarily stopped for each rotation at the specified angle and image capturing on the entire culture medium surface of the petri dish is performed.

4. The process according to claim 1, wherein n is four, five, or six.

5. A process for using an imaging apparatus to count the number of colonies on a culture medium surface comprising the steps of:
positioning a petri dish having a culture medium and a colony to be counted in an imaging apparatus;
imaging the entire culture medium surface of the petri dish using the imaging apparatus;
rotating the image capturing apparatus around a rotational axis by 360/n degrees, where n is a positive integer;
imaging the entire culture medium surface of the petri dish with the imaging apparatus at that rotational position;
repeating the rotating and imaging steps n−1 times;
processing the image data of the entire culture medium surface of the petri dish to count the number of colonies, wherein a counting region for the counting the number of colonies is determined to be the whole petri dish inside the side wall, and the number of colonies in the counting region at a specified angle is counted and acquired;
acquiring a colony count value for each of the n entire culture medium surface images; and
combining and averaging the number of colonies counted for each of the entire culture medium surface images in the petri dish to obtain a colony count for the culture medium surface within the petri dish.

6. The process according to claim 5, wherein when image capturing is performed on the entire culture medium surface of the petri dish at each specified angle,
the imaging apparatus performs image capturing a plurality of times per specified angle and acquires a plurality of images at each specified angle;
data processing is performed on each acquired image data to count the number of colonies at each specified angle a plurality of number of times; and
numerical processing is performed on the number of colonies counted separately at each specified angle to calculate the number of colonies in the petri dish.

7. The process according to claim 5, wherein the image capturing means is temporarily stopped for each rotation at the specified angle and image capturing on the entire culture medium surface of the petri dish is performed.

8. The process according to claim 5, wherein n is four, five, or six.

* * * * *

UNITED STATES PATENT AND TRADEMARK OFFICE
CERTIFICATE OF CORRECTION

PATENT NO.        : 8,831,326 B2
APPLICATION NO.   : 12/601544
DATED             : September 9, 2014
INVENTOR(S)       : Takashi Nishida et al.

Page 1 of 1

It is certified that error appears in the above-identified patent and that said Letters Patent is hereby corrected as shown below:

In the Specification:

On column 5, line 27, delete "COD" and add --CCD--
On column 6, line 27, delete "COD" and add --CCD--
On column 6, line 30, delete "COD" and add --CCD--
On column 6, line 38, delete "COD" and add --CCD--
On column 14, line 56, delete "COD" and add --CCD--

Signed and Sealed this
Twenty-first Day of July, 2015

Michelle K. Lee
*Director of the United States Patent and Trademark Office*